US010209300B2

(12) United States Patent
Kotelyanskii et al.

(10) Patent No.: US 10,209,300 B2
(45) Date of Patent: Feb. 19, 2019

(54) OPTO-ACOUSTIC METROLOGY OF SIGNAL ATTENUATING STRUCTURES

(71) Applicant: Rudolph Technologies, Inc., Flanders, NJ (US)

(72) Inventors: Michael Kotelyanskii, Chatham, NJ (US); Roman Basistyy, Kearny, NJ (US)

(73) Assignee: Rudolph Technologies, Inc., Wilmington, MA (US)

( * ) Notice: Subject to any disclaimer, the term of this patent is extended or adjusted under 35 U.S.C. 154(b) by 86 days.

(21) Appl. No.: 15/346,278

(22) Filed: Nov. 8, 2016

(65) Prior Publication Data

US 2017/0141004 A1    May 18, 2017

Related U.S. Application Data

(60) Provisional application No. 62/254,587, filed on Nov. 12, 2015.

(51) Int. Cl.
| | |
|---|---|
| *H01L 21/66* | (2006.01) |
| *G01R 31/302* | (2006.01) |
| *G01R 31/28* | (2006.01) |
| *H01L 21/768* | (2006.01) |
| *G01N 21/17* | (2006.01) |
| *G01N 21/95* | (2006.01) |

(52) U.S. Cl.
CPC ..... *G01R 31/3025* (2013.01); *G01N 21/1702* (2013.01); *H01L 21/7685* (2013.01); *H01L 21/76883* (2013.01); *H01L 22/12* (2013.01); *G01N 21/9501* (2013.01)

(58) Field of Classification Search
None
See application file for complete search history.

(56) References Cited

U.S. PATENT DOCUMENTS

| | | | | |
|---|---|---|---|---|
| 5,444,637 | A | * 8/1995 | Smesny | B24B 37/013 257/E21.528 |
| 2013/0112974 | A1 | * 5/2013 | Bouchoucha | H01L 22/12 257/48 |
| 2015/0099973 | A1 | * 4/2015 | Abe | G01N 21/1702 600/440 |
| 2015/0204822 | A1 | * 7/2015 | Horan | G01N 29/2418 73/643 |

(Continued)

*Primary Examiner* — Angel Roman

(57) ABSTRACT

Methods and systems for manufacturing and analyzing interconnect structures in integrated circuit (IC) devices. The methods include forming an interconnect structure, such as a pillar, in an IC device. The pillar is analyzed using an opto-acoustic sensor to quantify physical characteristics used to determine whether the pillar satisfies predetermined quality criterion. The analysis includes capturing an opto-acoustic signal from the pillar and estimating optical parameters for a number of local maxima of the signal. A mode may then be fitted for each of the identified local maxima based on the optical characteristics. The modes and estimated optical parameters may then be iteratively corrected in an order from strongest to weakest local maximum. The corrected values may then be compared to a predicted physical model to identify the physical characteristics of the pillar. If the physical characteristics fall outside of the quality criterion, manufacturing processes may be altered.

16 Claims, 10 Drawing Sheets

(56) References Cited

U.S. PATENT DOCUMENTS

2016/0113507 A1* 4/2016 Reza ................. G01N 21/1717
                                                          356/477
2018/0168457 A1* 6/2018 Ebisawa .............. A61B 5/0095

* cited by examiner

| Frequency for Mode 1 (MHz) | Frequency for Mode 2 (MHz) | Radius (Micron) | Thickness (Micron) |
| --- | --- | --- | --- |
| 51.26953 | 35.8963 | 20.00 | 27.00 |
| 51.11694 | 36.16333 | 20.00 | 28.00 |
| 50.58289 | 35.8963 | 20.00 | 30.50 |
| 50.50659 | 35.9726 | 20.00 | 31.00 |
| 49.70551 | 34.48486 | 22.00 | 29.00 |
| 49.66736 | 34.56116 | 22.00 | 29.50 |
| 49.59106 | 34.63745 | 22.00 | 30.00 |
| 49.51477 | 34.71375 | 22.00 | 30.50 |
| 49.43848 | 34.79004 | 22.00 | 31.00 |
| 48.82813 | 33.76007 | 24.00 | 29.00 |
| 48.75183 | 33.83636 | 24.00 | 29.50 |
| 48.67554 | 33.87451 | 24.00 | 30.00 |
| 48.59924 | 33.95081 | 24.00 | 30.50 |
| 48.52295 | 33.98895 | 24.00 | 31.00 |
| 48.10333 | 33.22601 | 26.00 | 29.00 |
| 47.98889 | 33.26416 | 26.00 | 29.50 |
| 47.9126 | 33.30231 | 26.00 | 30.00 |
| 47.8363 | 33.34045 | 26.00 | 30.50 |
| 47.72186 | 33.3786 | 26.00 | 31.00 |
| 47.37854 | 32.76825 | 28.00 | 29.00 |
| 47.30225 | 32.76825 | 28.00 | 29.50 |
| 47.22595 | 32.8064 | 28.00 | 30.00 |
| 47.11151 | 32.84454 | 28.00 | 30.50 |
| 47.03522 | 32.88269 | 28.00 | 31.00 |
| 46.76819 | 32.38678 | 30.00 | 29.00 |
| 46.69189 | 32.38678 | 30.00 | 29.50 |
| 46.6156 | 32.42493 | 30.00 | 30.00 |
| 46.50116 | 32.46307 | 30.00 | 30.50 |
| 46.38672 | 32.46307 | 30.00 | 31.00 |

FIG. 6

OPTO-ACOUSTIC METROLOGY OF SIGNAL ATTENUATING STRUCTURES

RELATED APPLICATION

This application claims the benefit of U.S. Provisional Application No. 62/254,587, filed on Nov. 12, 2015, which application is hereby incorporated by reference.

INTRODUCTION

Over the years, manufacturers of integrated circuit (IC) devices have generally followed the trend described by Gordon Moore in the mid-1960's by continuously shrinking the size of their devices, increasing their speed and reducing their cost. Of late, the ever increasing cost of process equipment and fabrication facilities has made it difficult to maintain this trend. One solution to this growing difficulty that has gained popularity is the packaging of multiple IC devices in close proximity to one another to form a single package. While the individual IC devices may not themselves be smaller or faster, the packaging of multiple IC devices into a larger device which is faster or at least more inexpensive than a comparable single IC device is one way in which manufacturers have kept up with Dr. Moore's law.

In one packaging technology, interconnect structures, often including small pillars of conductive materials, are used to vertically stack individual IC devices as part of single package. These interconnect structures are used in lieu of wires to electrically and physically connect individual IC devices. As one might expect, even a single defective interconnect structure may render an IC package inoperable in the same way that a missing or disconnected wire would render a light switch inoperative. And, given that the packaging step is very near the end of the fabrication process, such a defect can result in a very high monetary loss as each end-stage failed device represents a relatively high sunk cost.

Accordingly, there is a need to accurately and quickly inspect and measure different characteristics of interconnect structures, such as pillars—a task which is often made more difficult by the structures of the pillars themselves.

OPTO-ACOUSTIC METROLOGY OF SIGNAL ATTENUATING STRUCTURES

Manufacturing an interconnect structure, such as a pillar, bump, or bond pad for an IC device, begins with forming the interconnect structure itself. This interconnect structure may be a pillar with a polymer or other dampening coating, conformal structure, rough surfaces, or other dampening characteristics. The interconnect structure is formed using any of a range of semiconductor device fabrication processes such as, for example, washing, coating, curing, exposing, developing, etching, depositing, inspecting and measuring.

The interconnect structure is measured using an opto-acoustic sensor. The resulting signal is analyzed to quantify physical characteristics of the interconnect structure and to determine whether the interconnect structure meets some quality criterion, e.g., is within design specifications. If the interconnect structure is not within the design specifications, then the aforementioned processes may be modified such that subsequent interconnected devices are more likely to meet specifications or possibly a defective interconnect structure may be reworked to salvage the investment that might otherwise be lost.

Analyzing interconnect structures such as pillars that have damping coatings or structures around them may involve capturing from the pillar using the opto-acoustic sensor a plurality of opto-acoustic signals and then identifying from the captured opto-acoustic signals one or more local maxima that are correlated to candidate modes that are likely to be associated with a physical characteristic of the pillar. Based on estimates of the optical properties, a mode can be fitted for each of the identified local maxima. Those fitted modes are then iteratively corrected in an order from strongest to weakest associated local maximum to generate a set of corrected data and corrected optical parameters. The corrected data and corrected optical parameters can be compared to a predicted physical model to identify physical characteristics of the analyzed interconnect structure. Where the interconnect structure is a pillar, the measured physical characteristics of the interconnect structure may be a diameter or radius of the pillar, a thickness of a pillar cap, and/or a thickness or depth of the pillar. Other characteristics may also be measured based on the predicted physical models. These characteristics may include stresses/strains in the interconnect structure and the presence of voids or cracks in an interconnect structure.

The opto-acoustic system may be an interferometer of a type suitable to carry out opto-acoustic measurements. The opto-acoustic system may also be a system along the lines of the MetaPULSE or SONUS opto-acoustic metrology systems available from Rudolph Technologies, Inc. of Flanders, N.J.

BRIEF DESCRIPTION OF THE DRAWINGS

FIG. 6 depicts an example table from a predicted physical model.

DETAILED DESCRIPTION

Figure 1:
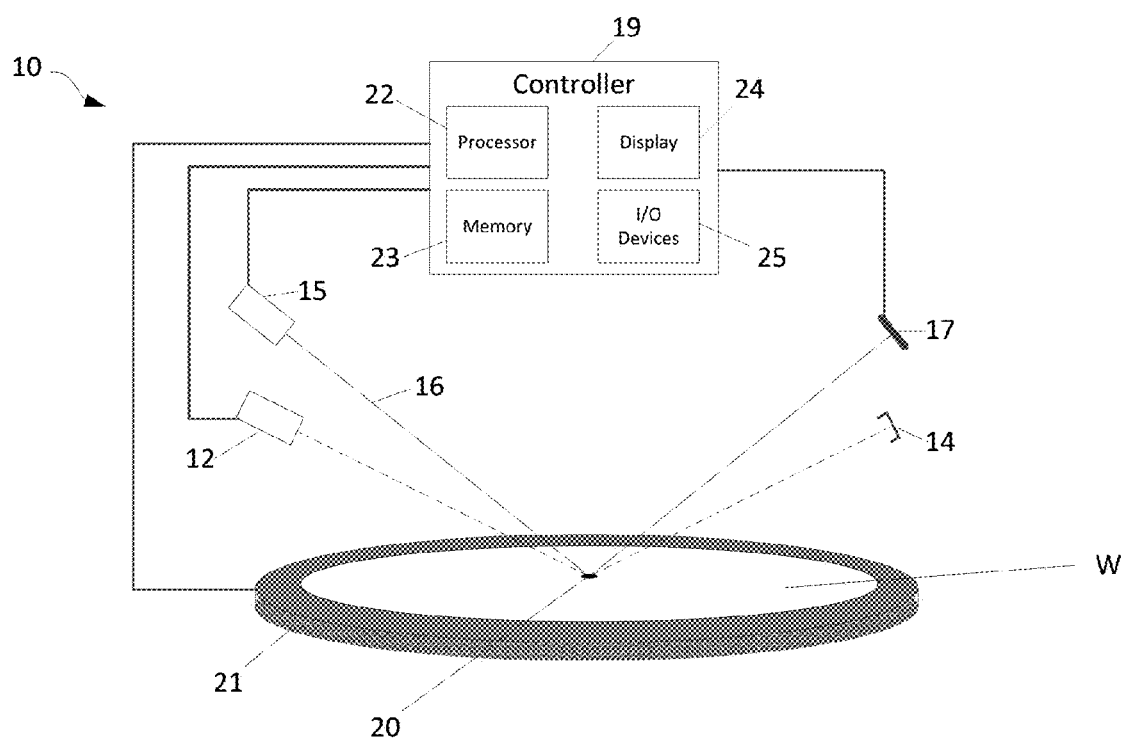
FIG. 1 is a schematic illustration of a opto-acoustic measurement system being addressed to a feature on a wafer.

In the following detailed description, reference is made to the accompanying drawings that form a part hereof, and in which is shown, by way of illustration, specific embodiments in which the technology may be practiced. In the drawings, like numerals describe substantially similar components throughout the several views. These embodiments are described in sufficient detail to enable those skilled in the art to practice the technology. Other embodiments may be utilized and structural, logical, and electrical changes may be made without departing from the teaching provided in this disclosure. The following detailed description is, therefore, not to be taken in a limiting sense.

Generally, semiconductor metrology involves the measurement of features that are small enough to make it difficult to sense the features directly. Accordingly, it is common practice to generate, a priori, a model of how a structure being measured will respond to a particular stimulus. In fact, multiple models, each positing a slightly different response based on a slightly different nominal structure, are generated. Thereafter, actual measurements are taken and compared with the models. Interpolation and fitting methods are used to identify which model best fits the actual measurements. The physical characteristics, often physical dimensions but other criteria may be used, are taken from the model to be those that best fit the observed measurements. This process works well when an opto-acoustic signal representing a strong, minimally attenuated acoustic wave can be generated from measurement. Many structures, however, have features that cause significant dampening or attenuation of the acoustic wave. Where measurement signals from such structures are weak, are subject to a great deal of noise, or decay or are damped rapidly, difficulty arises in attempting to accurately parse the signal to generate usable results. The present technology provides solutions that allow for extraction of usable data from rapidly attenuated data signals that allow for a determination of the physical characteristics of an interconnect structure, such as a pillar, to be determined. For example, the present technology estimates a number of modes from rapidly attenuated data and iteratively fits and corrects the mode estimates to generate corrected data that is suitable to be compared to a predicted physical model.

FIG. 1 depicts an embodiment of an opto-acoustic system 10 that may carry out measurements for the present technology. In the Figure, the opto-acoustic system 10 is addressed to a feature 20 formed as part of a wafer W. The wafer W shown in this Figure is a generic representation of a substrate of a type commonly used in IC fabrication. Wafers or panels made from silicon, gallium arsenide, germanium, sapphire, resins, and conglomerates of the foregoing or other similar materials may form a suitable substrate. Further, it is to be understood that the wafer W may represent portions of a substrate or all or a portion of a conglomerate of substrates, e.g., a reconstituted substrate with multiple IC devices or portions of IC devices commonly used in processes known to those skilled in the art as "advanced packaging".

Figure 2:
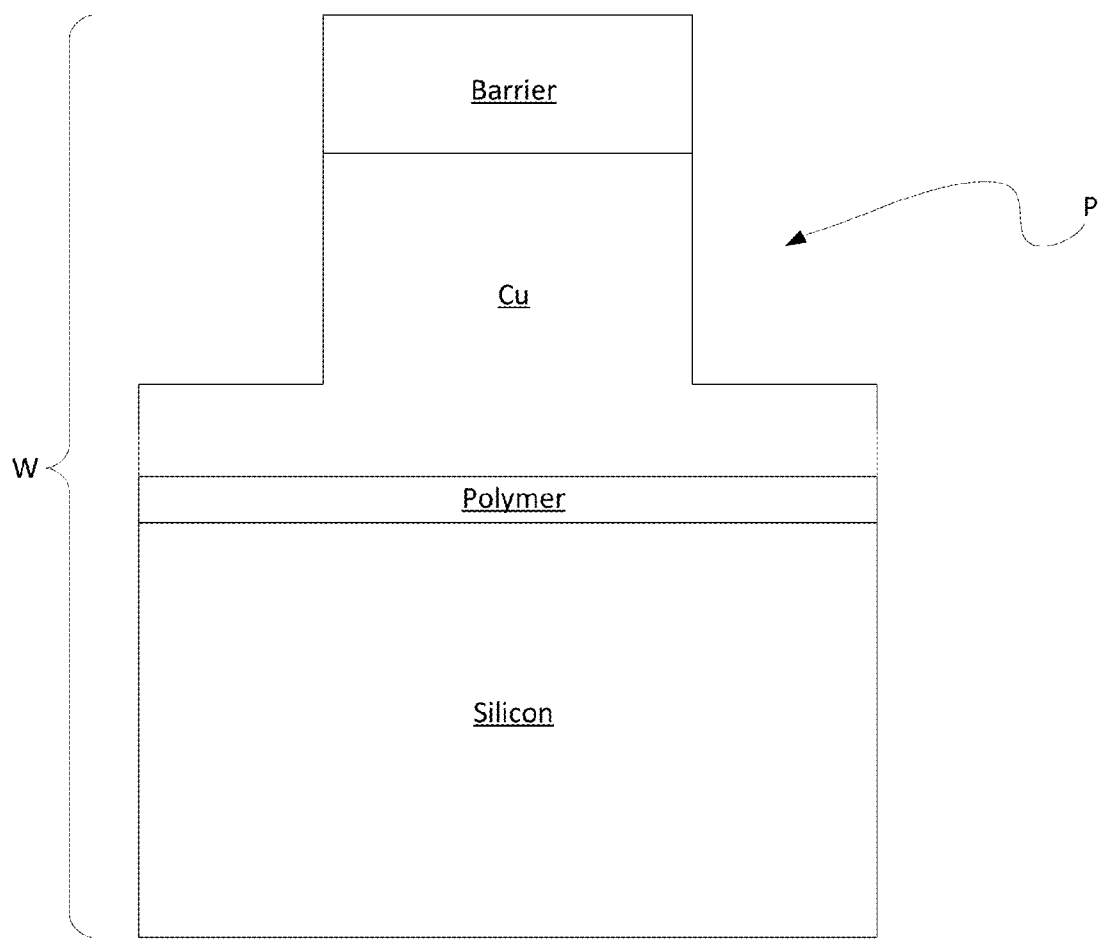
FIG. 2 illustrates an example interconnect structure.

The feature 20 may be any identifiable physical element in the wafer W, such as an interconnect structure. For example, the feature 20 may be a pillar, solder bump, via, nail, column or the like. Below, the measurement technology will be described as used in the measurement of an interconnect structure in the form of a pillar P which is described in more detail in conjunction with FIG. 2, although the reader will understand that the technology may be used for measurement of any physical feature on the wafer W. Pillars P, in general, are simply a columnar structure of electrically conductive material. FIG. 2 shows an exemplary pillar P shown in a simplified fashion. Pillars P may be formed with various resists, encapsulants, dielectrics or coatings in close conformity with their side walls (not shown). Of importance is the fact that measurements of characteristics of a pillar P using an opto-acoustic measurement system 10 can be difficult. This difficulty is emphasized where encapsulants, coatings, dielectrics, or layers cause acoustic signals induced in a pillar P to be damped out relatively quickly.

The exemplary pillar P shown in cross section in FIG. 2 is formed of multiple layers. In this particular embodiment the pillar P has a barrier layer at its top that may be made of conductive metallic material such as tin-silver (SnAg) or nickel (Ni). The body of the pillar P is often formed of copper (Cu), though other materials such as aluminum may be used. In the given example, the copper body overlies a polymer layer which in turn rests upon the silicon body of a wafer W. Those skilled in the art will recognize that this pillar P represents but one feature 20 that may exist on a wafer W. Further, it will be understood that other pillar P structures, dimensions, aspect ratios, and composition are possible and well-known in the art.

The opto-acoustic system 10 shown in FIG. 1 operates based on thermo-acoustic principles. In measuring a feature 20, such as an interconnect structure, a pump beam 13 of light or radiation is emitted by a source 12 onto the feature 20 to be measured. The pump beam 13 is at least partially absorbed into the surface of the feature, thereby quickly heating the surface of the feature. This quick heating creates a rapid expansion of the material of the feature 20, inducing acoustic waves in the feature 20 itself. The acoustic wave passes into the feature 20 and is at least partially reflected back to the surface of the feature by structures within the feature 20, including reflections from the interfaces between the layers of the interconnect structure, such as pillar P. For example, as with sonar, successive portions of the acoustic wave moving from the surface of the feature 20 down through the pillar P are reflected by the interface between each layer of the pillar P. Another portion of the acoustic wave is reflected from the bottom of the pillar P. Note that the portion of the pump beam 13 that is not absorbed by the feature 20 is reflected to a beam dump 14, also known as a photon motel.

In some examples, at predetermined periods of time after the pump beam 13 is incident on the feature 20, probe beams 16 of light or radiation are directed from a source 15 onto the feature 20 that is being measured. In other examples, the probe beam 16 is a continuous beam and a time-dependent signal is recorded by the sensor 17. These probe beams 16 sense changes in the reflectivity of the surface of the feature 20 at predetermined time delays that correspond to the position of the interfaces within the feature 20. The probe beam 16 may also sense small perturbations in the shape of the surface at the predetermined times. Changes in reflectivity and perturbations in the surface of the feature 20 are encoded in the probe beam 16 sensed by a sensor 17.

A controller 19 is connected to the sources 12, 15, to the sensor 17 and to a stage 21 which supports and moves a wafer W to a predetermined series of positions at which the pump and probe beams of light or radiation 13, 16 intersect with the feature 20 that is under test. The controller 19 directs the operation of the sources 12, 15, receives the output of the sensor 17 and positions the stage 19 appropriately. Depending on the manner in which the opto-acoustic system 10 is constructed and arranged, the controller 19 may be used to create, store, and implement models of the feature 20 that is under test which may be used to decode measurement values from signals output by the sensor 17.

The controller 19 includes at least one processor 22 and a memory 23 that stores instructions that are executable by the at least one processor 22 to performs operations forming methods or processes, such as the operations discussed below in FIGS. 5A-5C. For example, the processor 22 may be a multi-purpose processor or a dedicator processor specific to the particular execution requirements for the particular functions to be performed. The memory 22 may also be a multi-purpose memory, firmware or other dedicated memory, or a combination thereof. The processor 22 and memory 23 may be incorporated in combination as a part of a multi-purpose computer or within a field-programmable gate array (FPGA) or another application-specific integrated circuit (ASIC). The controller 19 may also include a display 24 for displaying results of measurements or other features resulting from execution of the operations. Additional input/output (I/O) devices 25 may be incorporated into or attached to the controller 19 to allow for additional inputs and outputs to be received and sent from the controller 19. The controller 19 may further include an operating system stored within the memory 22 to control the resources of the controller 19 and the processes using those resources.

FIG. 2 illustrates an example interconnect structure in the form of a pillar P. Opto-acoustic signals obtained from structures such as pillars P can be difficult to detect and parse into accurate measurements when the structure to be measured has elements or characteristics that dampen the acoustic wave's propagation through the structure. In some examples, the dampening or attenuation may be caused by polymer materials surrounding the pillar P. For instance, a polymer resist may surround the pillar or may be present as a contaminating residue at the top of the pillar or in other locations. In other examples, the attenuation may be exacerbated or substantially due to surface roughness of the pillar sidewalls or the top of the barrier. Inhomogeneous grain structure in the metal layers, such as in a SnAg alloy forming the barrier or in copper layers. Roughness and microphase formations at the inter-layer interfaces may also contribute to the dampening. In examples with high attenuation of the acoustic wave, the results of the conventional measurement techniques are often equivocal.

Figure 3A:
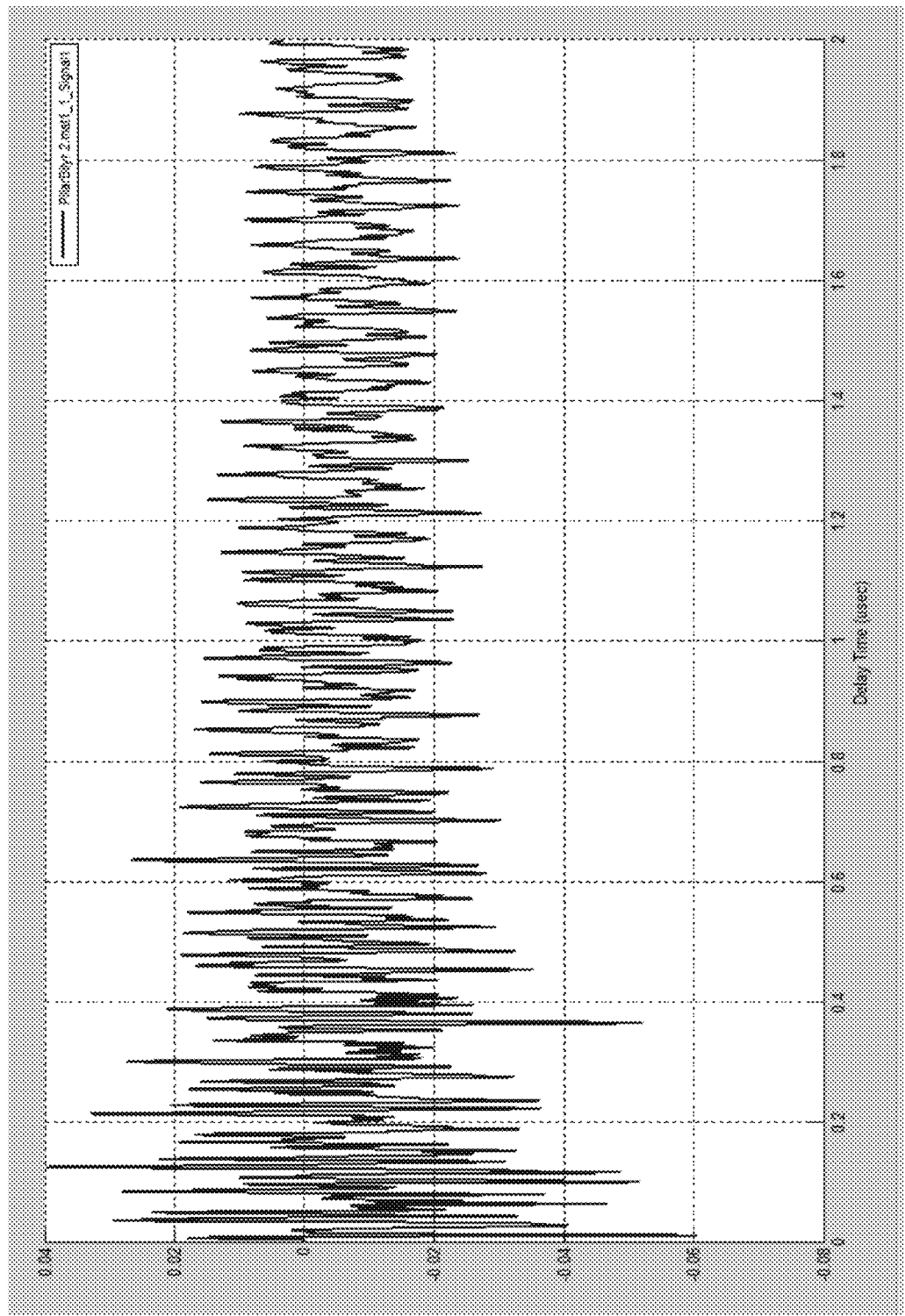
FIG. 3A shows a plot of a time-dependent signal from opto-acoustic analysis of an interconnect structure without significant dampening features or characteristics.
Figure 3B:
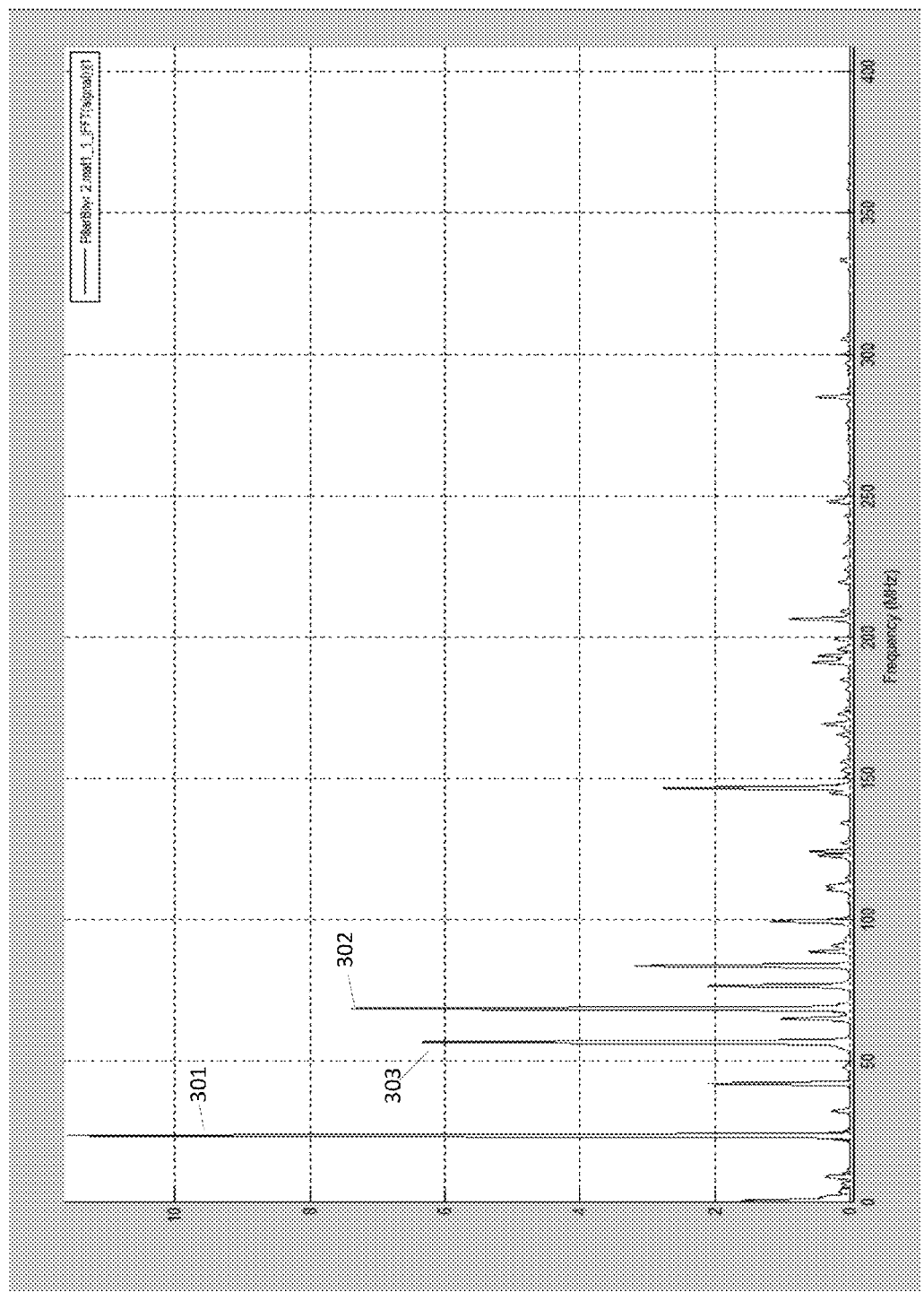
FIG. 3B shows a plot of a Fourier transform of the signal shown in FIG. 3A.

In embodiments of an interconnect structure, such as pillar P, without the dampening features or characteristics discussed above, acoustic waves typically propagate over relatively longer time frames which may be on the order of 1-2 microseconds or more. FIG. 3A shows a plot of a time-dependent signal from opto-acoustic analysis of such an interconnect structure without the dampening features or characteristics discussed above. FIG. 3B shows a plot of a Fourier transform of the signal shown in FIG. 3A. As can be seen in FIG. 3B, the plot includes strong peaks that are indicative of vibrational modes of the acoustic wave. For example, the three strongest modes are identified on the plot as mode 301, mode 302, and mode 303. Mode 301 has an amplitude over 10 and a frequency of approximately 25 megahertz (MHz). The amplitude shown in the plots are proportional to the surface displacement at the location of the probe beam. Mode 302 has an amplitude of approximately 7.2 and a frequency of approximately 70 MHz. Mode 303 has an amplitude of approximately 6.5 and a frequency of approximately 60 MHz. The strong peaks in the Fourier transform depicted in FIG. 3B are indicative of modes due to their tight band around a particular frequency and high amplitudes. These identified modes are well-suited for comparison to a predicted physical model to determine the physical characteristics of the analyzed interconnect structure.

Figure 4A:
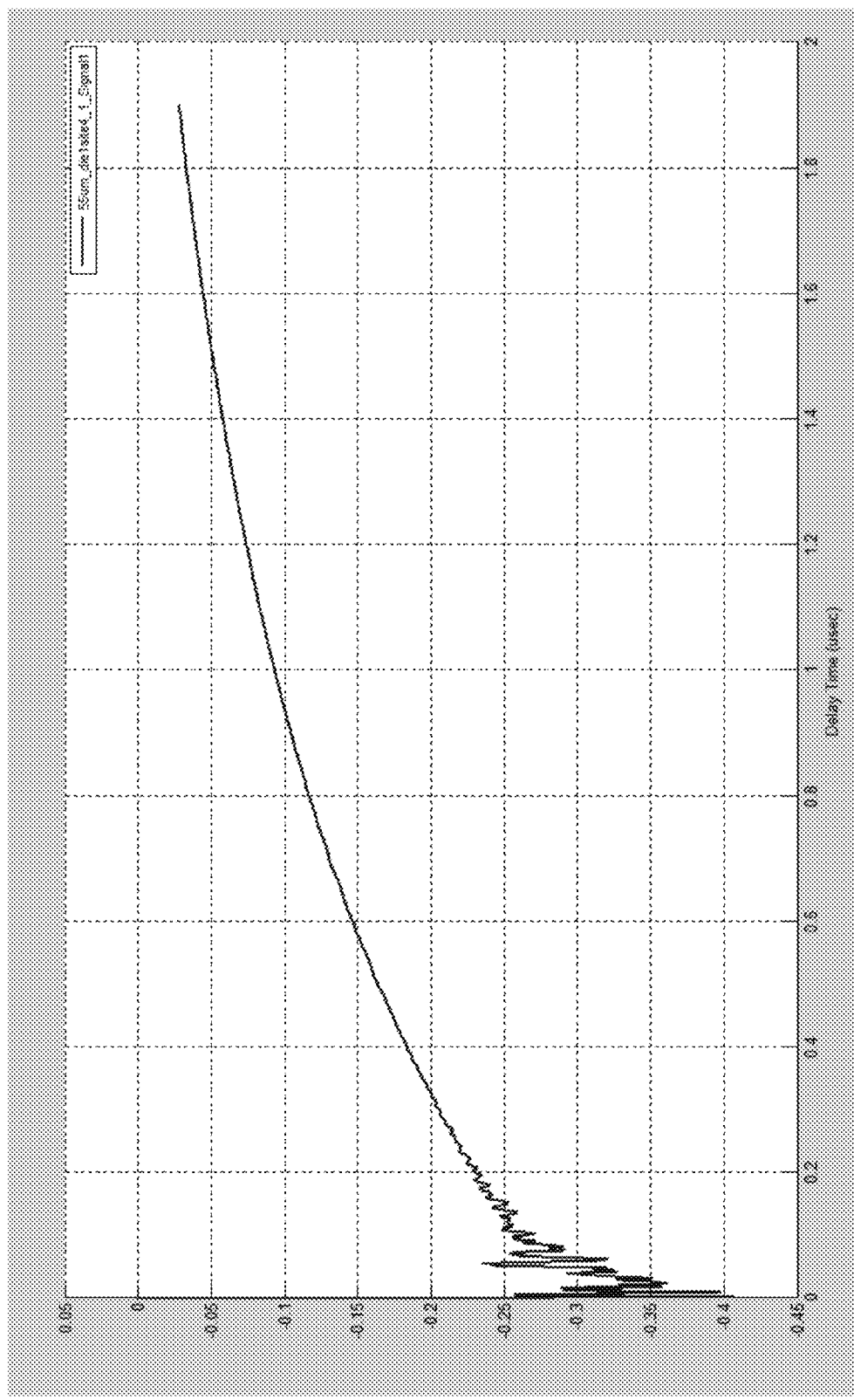
FIG. 4A shows a plot of a time-dependent signal from opto-acoustic analysis of an interconnect structure with significant dampening features or characteristics.

Conversely, FIG. 4A shows a plot of a time-dependent signal from opto-acoustic analysis of an interconnect structure with the dampening features or characteristics discussed above. As can be seen from FIG. 4A, the signal is damped quickly. In the example depicted, acoustic waves propagating within a pillar P are damped out within about 0.3 microseconds. It is to be understood that the damping nature of structures being measured vary and that the time frames given in the preceding examples may be shorter or longer for any given structure.

Figure 4B:
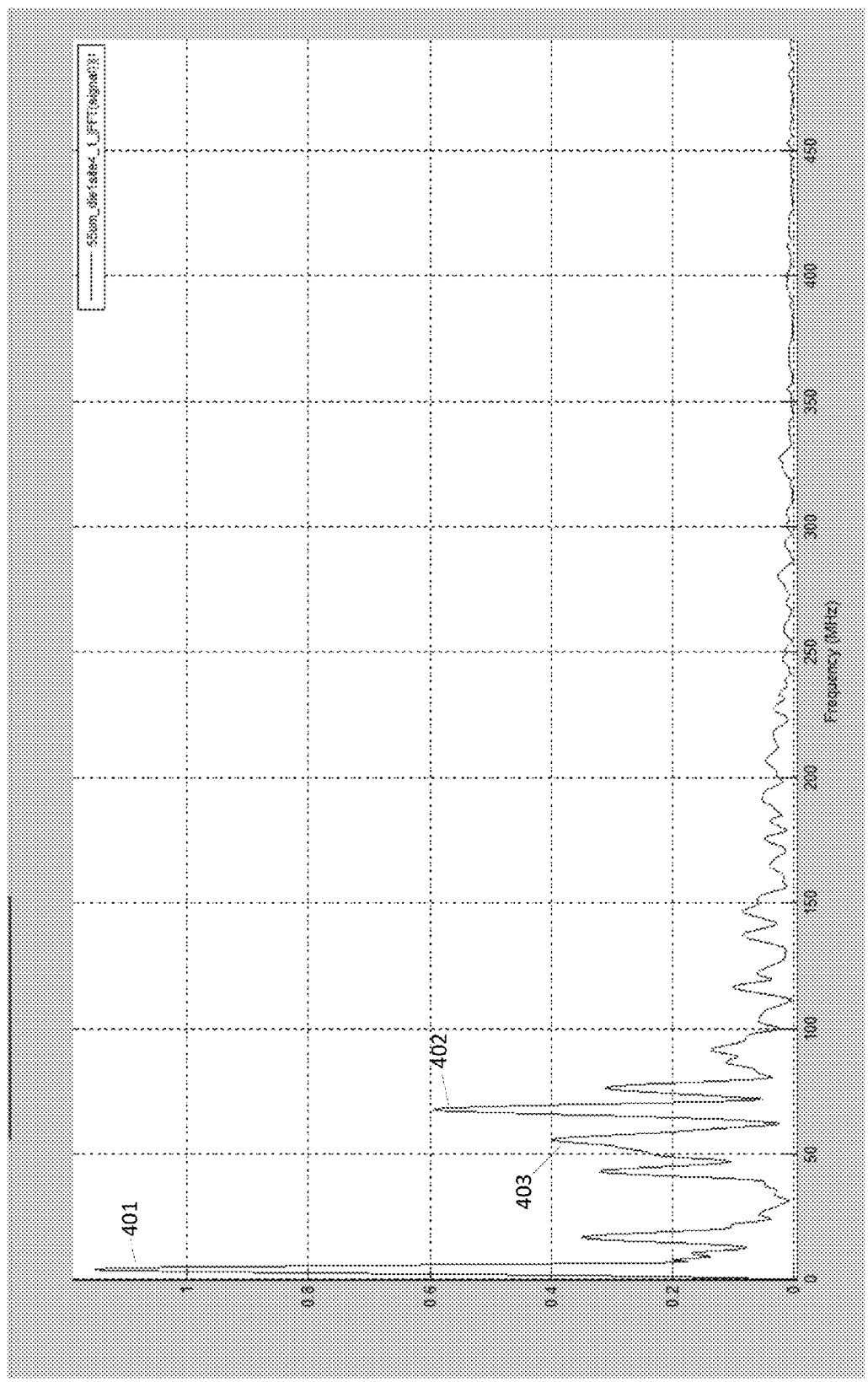
FIG. 4B shows a plot of a Fourier transform of the of the signal shown in FIG. 4A.

Because of the quickly damped signal, a Fourier analysis alone is not well-suited for meaningful analysis of the damped signals because accurate estimates of the vibrational modes cannot be determined solely from the Fourier analysis. For instance, the acoustic signals returned or reflected from portions of the interconnect structure, such as boundaries or interfaces, being measured are of generally low amplitude and do not have tight frequency bands. As an example, FIG. 4B shows a plot of a Fourier transform of the signal shown in FIG. 4A. As compared to the Fourier transform depicted in FIG. 3B, the Fourier transform in FIG. 4B does not exhibit the same high-amplitude, tight-banded peaks. While some local maxima can be identified, such as local maximum 401, local maximum 402, and local maximum 403, identification of those local maxima alone provide less-accurate estimates of vibrational modes of the acoustic wave. With the use of the present technology, however, useable data and accurate measurements of physical characteristics can be extracted from such significantly damped acoustic signals propagating in interconnect structures with dampening elements or structures.

Figure 5A:
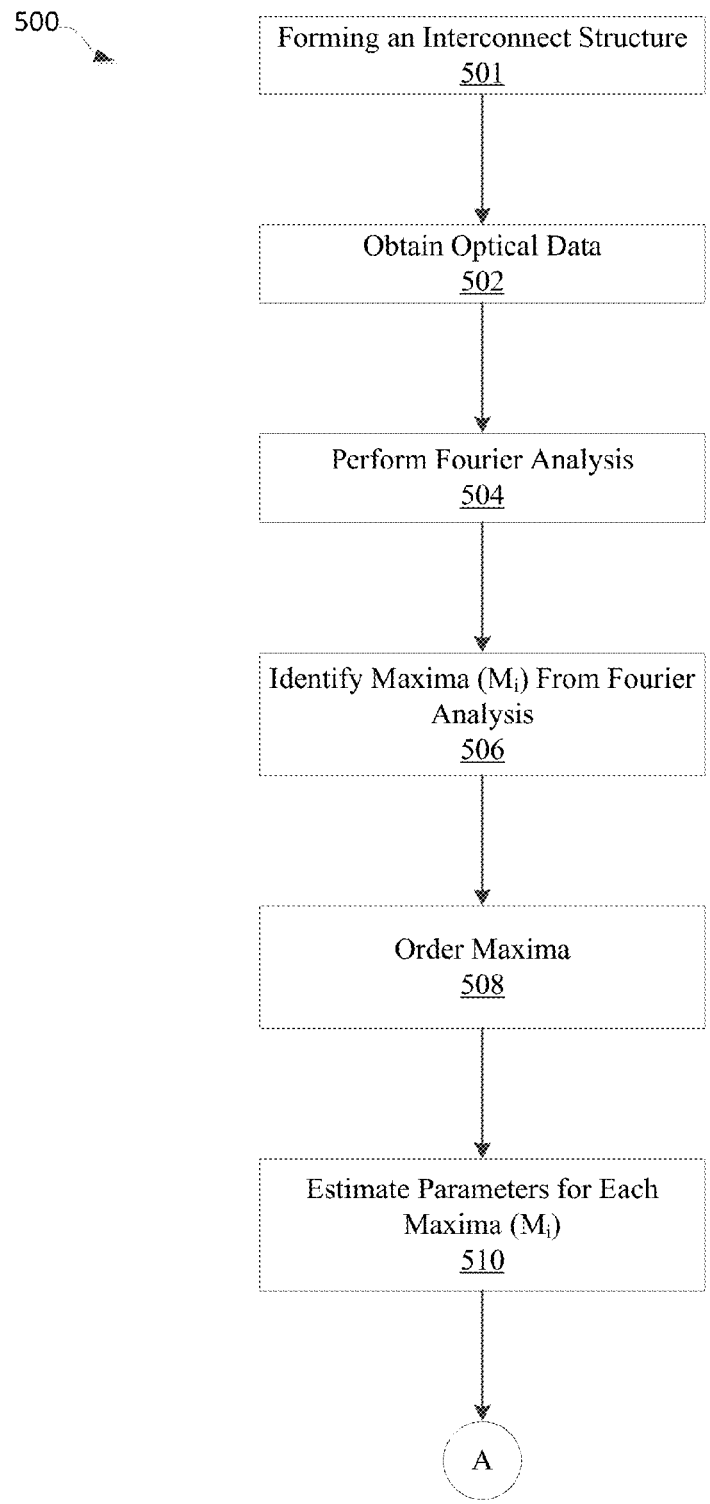
FIGS. 5A-5C depict an example method for measurement of physical characteristics of an interconnect structure such as a pillar.
Figure 5B:
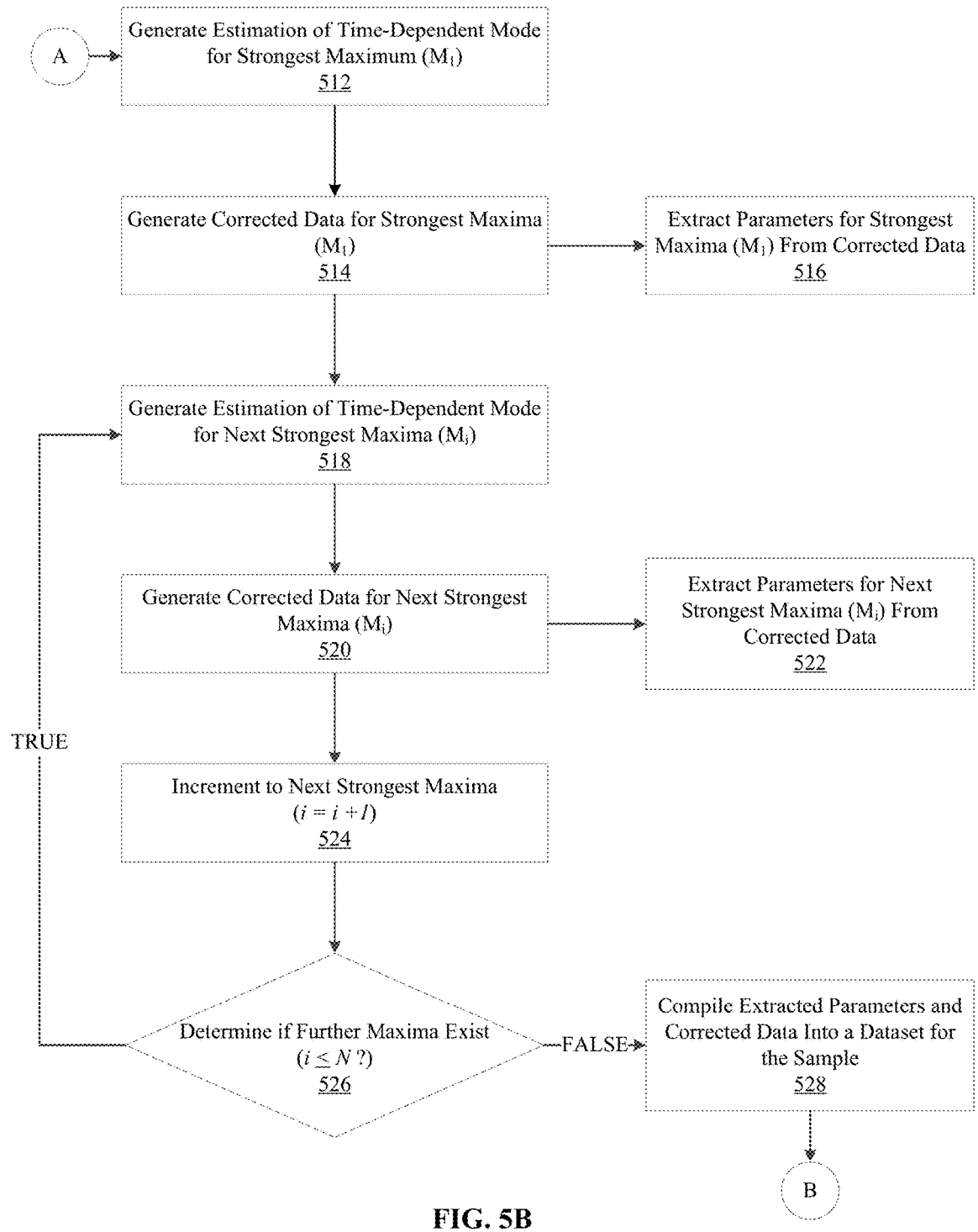
Figure 5C:
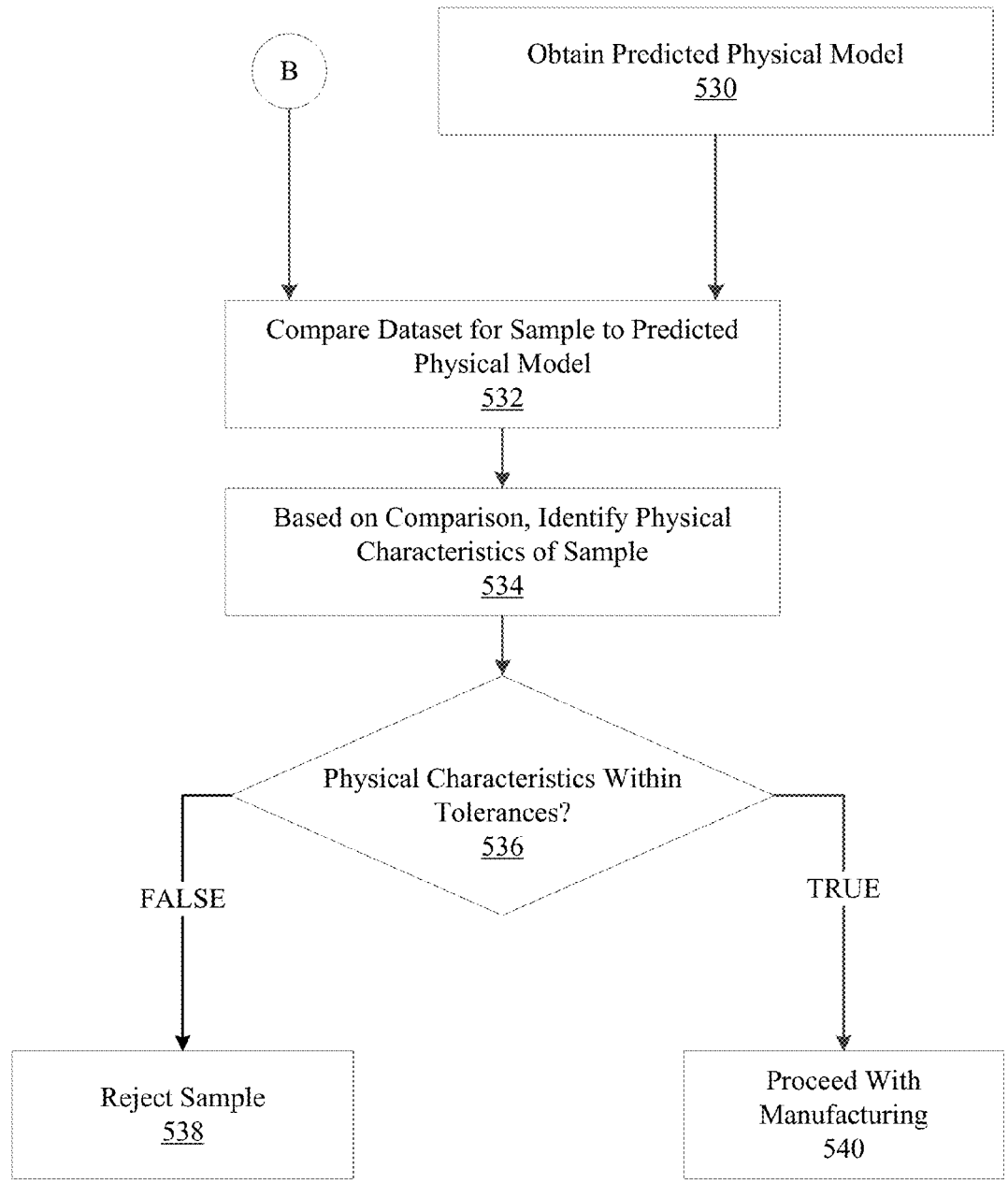

FIGS. 5A-5C depict an example method 500 for measurement of physical characteristics of an interconnect structure such as a pillar. The method 500 may also be a part of a method for manufacturing an interconnect structure in an IC device. The method 500 may be performed as an intermediate step in the IC device manufacturing process, such as after each interconnect structure or set of structures are created. Likewise, as part of the overall manufacturing process the method 500 may be performed on all, some, or just one of the interconnect structures on the wafer W.

The method 500 begins at operation 501 where an interconnect structure is formed in an IC device. In other examples, a sample wafer may be received having an already formed interconnect structure at operation 501.

Optical data are generated by directing pump and probe beams from the interconnect structure, as described above, at operation 502. At operation 502, optical data are obtained from a sensor, such as sensor 17 in FIG. 1. The optical data may be opto-acoustic data obtained from an opto-acoustic system such as the one depicted in FIG. 1. For example, the optical data obtained at operation 502 may be similar to the time-dependent opto-acoustic signal shown in the plots in FIGS. 3A and 4A. In some instances, mode tracing techniques are used to smooth the acoustic signal.

At operation 504, a Fourier analysis, or similar technique, is performed on the optical data received at operation 502 to generate a dataset or plot similar to the plots in FIGS. 3B and 4B.

At operation 506, a plurality of local maxima in the Fourier-transformed dataset generated in operation 504 are identified. The plurality of local maxima may be identified by any functions or techniques suitable for determining local maxima in a dataset or plot, such as techniques based on a change in sign of a first derivative of a non-linear function representative of the Fourier-transformed data. The number of local maxima or peaks (N) that are identified at operation 506 may be equal to or greater than the number of physical characteristics that are desired to be determined by the present technology. Where too few peaks are selected, subsequent operations for identifying physical characteristics may fail. If too many peaks are selected, subsequent fitting steps will become more computationally expensive and the included noise may degrade the efficacy of the resulting physical characteristic measurements. In some instances, it has been found that setting N to the following values has been useful: $2 \leq N \leq 40$, $2 \leq N \leq 4$, $3 \leq N \leq 10$, $5 \leq N \leq 15$, or $10 \leq N \leq 20$. Other values may be appropriate in certain circumstances.

At operation 508, each of the identified local maxima are ordered by strength. The relative strength may be based on an amplitude of each of the local maxima. In some examples, the relative strength may be based on both the width the peak associated with the local maxima as well as the amplitude. In ordering the local maxima, each of the local maxima may be assigned an index number i. For instance, the strongest local maximum may be assigned an index number i=1, and the next strongest local maximum may be assigned an index number i=2. Each local maximum may be referred to as $M_i$, where the index number i indicates the order of the respective local maximum according to strength.

At operation 510, estimates of the optical parameters for each of the identified local maxima ($M_i$) are generated. The estimates of the optical parameters may be extracted from the time-dependent opto-acoustic signal and/or the Fourier-transformed dataset. The optical parameters may include one or more of the amplitude (A(i)), frequency (f(i)), phase ($\delta$(i) and attenuation or decay coefficient ($\gamma$(i))) for each local maximum $M_i$. These estimates may be obtained in one embodiment from the information provided from the Fourier transform used to create the plot in FIG. 4B. For instance, the amplitude and frequency can be directly extracted from a plot of the Fourier-transformed data, such as the plot in FIG. 4B. The phase can be extracted from the complex component of the Fourier-transform, and the attenuation or decay coefficient may be determined based on the width of the corresponding peak of the respective local maximum $M_i$. Other techniques for extracted estimates of such optical parameters as known by those having skill in the art may be utilized.

Estimates for time-dependent modes are generated for each of the N identified local maxima. For instance, at operation 512, an estimate for a time-dependent mode for the strongest local maximum ($M_1$) is generated based on the estimated optical parameters. In an example, the mode may be fit the form:

$$A(i)e^{-\gamma(i)t}\sin(f(i)t+\delta(i)) \quad (1)$$

In such an example, the elements of the above equation correspond to the estimated optical parameters determined in operation 510. In other examples, various fitting techniques may be used to fit the respective modes, including non-linear fitting techniques such as the Levenberg-Marquardt.

Corrected data for each of the local maxima are then iteratively generated in descending order from strongest local maxim ($M_1$) to the least strong maximum ($M_N$). For instance, at operation 514, corrected data for the strongest local maximum ($M_1$) is generated. In one example, using the measured data as a fundus, error from each i of the N estimates obtained as described above is removed. Because the optical signal may be thought of as a superposition of all its underlying modes, corrected data can be generated for each mode by subtracting other modes from the signal. For instance, the corrected data may be generated according to the following regression equation:

$$data(i)=data(i-1)-A(i)e^{-\gamma(i)t}\sin(f(i)t+\delta(i)) \quad (2)$$

where data(i) is the corrected estimate. Note that for the strongest local maximum ($M_1$), the value data(0) may be the measured signal obtained in operation 502. Accordingly, in some examples, the data(i) may be a set of data or may be a non-linear equation. At operation 516, corrected optical parameters may be extracted from the corrected estimate data(i). For example, corrected values for one or more of the amplitude A(i)), frequency (f(i)), phase ($\delta$(i)) and attenuation or decay coefficient ($\gamma$(i)) may be extracted from the corrected estimate.

The iterative process then continues to the next strongest local maximum ($M_2$) as illustrated by operations 518-526. At operation 518, an estimate for a time-dependent mode for the next strongest local maximum ($M_2$) is generated and may be fit to the same form as Equation 1 above. At operation 520, corrected data is generated for $M_2$ using Equation 2 above. As an example, the fitted mode for $M_2$ generated at operation 518 is subtracted from the corrected estimate for the strongest mode (data(1)) to generate the corrected estimate for $M_2$ (data(2)). At operation 522, corrected optical parameters may be extracted from the corrected estimate data(2), including one or more of the amplitude A(i)), frequency (f(i)), phase ($\delta$(i)) and attenuation or decay coefficient ($\gamma$(i)).

The iterative process is continued until each local maximum i of the total number of local maximums N have been processed. As an example for completing the iterative process, at operation 524, the index value i is incremented by one and a determination is made at operation 526 as to whether the index value i is less than or equal to the total number of local maxima N. If the index value i is less than or equal to N, the process flows back through operations 518-526 to fit a mode for the next strongest local maximum, generate a corrected estimate, and extract corrected optical parameters. If corrected estimates have already been generated (i.e., i>N), the process flows to operation 528 where the extracted corrected parameters and the generated corrected data may be compiled into a dataset representing the measurements for the sample.

A predicted physical model is obtained at operation 530. The predicted physical model is a model, set of values, or some other mathematical representation of the known or theoretical physical characteristics of an interconnect structure being measured. For example, finite element analysis (FEA) may be performed on a set of physical parameters of known interconnect structure to generate a table of values for theoretical optical parameters that should be observed upon analysis with an opto-acoustic system. For instance, the predicted frequencies of modes may be indicative of particular thicknesses, materials or diameters of an interconnect structure.

As a specific example, FIG. 6 depicts an example table from a predicted physical model generated from a finite element analysis. The predicted physical model depicted in FIG. 6 is for a pillar having only one layer, and the predicted physical model in FIG. 6 can be used to determine pillar radius and thickness of the layer. The first column of the table represents frequencies for a first mode and the second column of the table represents frequencies for a second mode. The third and fourth columns represents the radius of the pillar and the thickness of the layer, respectively. Accordingly, the table can be used to identify a radius and a thickness of a measured pillar when two modes can be identified in the optical data of a measured pillar. For instance, where the first identified mode has a frequency of approximately 51.26953 MHz and the second identified mode has a frequency of approximately 35.8963 MHz, the pillar being measured has a radius of approximately 20.00 microns and a thickness of approximately 27.00 microns, as provided for in row one of the table. In other examples, the predicted physical model may be a non-linear time-dependent curve known to represent particular physical characteristics.

At operation 532, at least a portion of the dataset created at operation 528 is compared to the predicted physical model obtained in operation 530. If the predicted physical model is a table or similar model representing the predicted optical parameters for a particular structure, such as the table in FIG. 6, the predicted physical model is compared to the extracted corrected optical parameters stored in the data set. If the predicted physical model is a set of non-linear curves or similar data, the actual corrected data (e.g., data(i)), can be compared to the predicted physical model to determine the best fit. Other combinations or comparisons are also possible. At operation 532, the physical characteristics of the interconnect structure being analyzed may be identified based on the comparison in operation 532.

As an example of the process, a corrected frequency for respective local maxima may be identified from the corrected optical parameters extracted at operation 516 and 522. Those frequencies may then be compared to columns one and two in the table of predicted physical model shown in FIG. 6. For instance, the corrected frequency for $M_1$ and $M_2$ may be 48.82813 MHz and 33.76007 MHz, respectively. Comparing those frequencies to the frequencies in columns one and two of the tables, it is seen that row 10 includes a match for those two frequencies. Thus, the physical characteristics for the analyzed pillar are that the pillar has a radius of about 24 microns and a thickness of about 29 microns. Other matching and comparison techniques may be implemented.

At operation 536, the physical characteristics identified in operation 534 are compared to tolerances or other specifications to determine whether the interconnect structure being analyzed is acceptable. In an embodiment, the tolerances may take the form of an acceptable range of deviation from a specified vale for a particular parameter, e.g., within 1%, 2%, 5% or 10% of the specified value for the parameter. Different parameters may have different tolerances.

If the physical characteristics are within the tolerances, specifications, or other quality criterion, the interconnect structure is deemed acceptable and manufacturing of the IC device continues. For instance, fabrication processes involved in manufacturing such as washing, coating, curing, exposing, developing, etching, depositing and/or or further inspection and measurement will continue at operation 540. If the physical characteristics are not within the tolerances or specifications, manufacturing of the IC device including the interconnect structure is stopped and the sample may be rejected at operation 538. Operation 538 may also include, based on the obtained measurements of the physical characteristics, modifying or altering fabrication processes such as coating, bake, exposure, etching, deposition, and planarization steps used in the fabrication of subsequent semiconductor devices. Accordingly, improved accuracy and precision in the measurement of features of a substrate permit the processes whereby such substrates are produced to be more tightly controlled. Individual devices having defective features may be identified early in the fabrication process, thereby preventing defective devices from receiving additional costly processing or worse, inclusion in an electronic device that may fail as a result. This type of control results in higher process yields and improved product quality.

In further examples, once the physical characteristics are determined for the analyzed feature, a new predicted physical model may be generated based on the opto-acoustic data received for the analyzed feature. For instance, the opto-acoustic data is now known to potentially be indicative of the determined physical characteristics. The new predicted physical model may then be used to predict the nature of a signal that would result from a given structure of a feature. The model may include any of a number of geometric characteristics such as diameters and depths, but may also provide a quantization of characteristics of the grain size of metals that are measured or the stress that a metal is under, or any other physical characteristics determined. Once the model has been completed, a subsequent measurement obtained by the opto-acoustic system may be used to obtain feature characteristics from the model directly without requiring the additional steps described above if the opto-acoustic signal substantially matches the new predicted physical model.

While various examples were provided above, the measurement technology is not limited to the specifics of the examples. Additional signal analysis techniques may be used to identify preliminary modes, determine physical characteristics, and generate models. Further, while the processes have generally described being directed towards an interconnect structure, the technology described herein may also be used to analyze other structures or features that cause rapid attenuation or decay in the resulting signals.

Although specific embodiments of the measurement technology have been illustrated and described herein, it will be appreciated by those of ordinary skill in the art that any arrangement that is calculated to achieve the same purpose may be substituted for the specific embodiments shown. Many adaptations of the technology will be apparent to those of ordinary skill in the art. Accordingly, this application is intended to cover any adaptations or variations of the technology.

What is claimed is:

1. A method of manufacturing an interconnect structure for an integrated circuit (IC) device, the method comprising:
   forming the interconnect structure in the IC device;
   receiving a time-dependent opto-acoustic signal for the interconnect structure;
   performing a Fourier analysis of the time-dependent opto-acoustic signal to generate a Fourier-transformed dataset;
   identifying a plurality of local maxima from the Fourier-transformed dataset;
   generating an estimate of one or more optical parameters for each identified local maximum in the plurality of local maxima;
   fitting a first mode to a strongest maximum of the plurality of local maxima;
   subtracting the first mode from the time-dependent opto-acoustic signal to generate a first corrected dataset;
   fitting a second mode to a second strongest maximum of the plurality of local maxima;
   subtracting the second mode from the first corrected dataset to generate a second dataset;
   comparing the first and second datasets to a predicted physical model;
   based on the comparison, quantifying one or more physical characteristics of the interconnect structure of the integrated circuit;
   determining whether the one or more physical characteristics are within tolerances for the interconnect structure; and
   if the one or more physical characteristics are not within the tolerances, altering a fabrication process.

2. The method of claim 1, wherein the one or more optical parameters include at least two of amplitude, frequency, phase, and attenuation.

3. The method of claim 1, wherein the estimate of the one or more optical parameters is derived from the Fourier-transformed dataset.

4. The method of claim 1, wherein fitting the first and second modes is based on at least the estimate of the one or more optical parameters.

5. The method of claim 4, wherein fitting the first mode comprises fitting the mode to the form of:

$$A(i)e^{-\gamma(i)}\sin(f(i)t+\delta(i)),$$

wherein A represents an amplitude, t represents time, $\gamma$ represents an attenuation, $\delta$ represents a phase, and i is an index value for the local maximum.

6. The method of claim 1, further comprising:
extracting a first set of corrected optical parameters for the first mode from the first corrected dataset; and
extracting a second set of corrected optical parameters for the second mode from the second corrected dataset.

7. The method of claim 6, wherein comparing the first and second datasets to a predicted physical model comprises comparing the first and second set of corrected optical parameters to the predicted physical model.

8. The method of claim 1, wherein the number of local maxima identified corresponds to the number of the one or more physical characteristics.

9. The method of claim 1, wherein corrected data sets for each of the remaining local maxima in the plurality of local maxima are iteratively generated in order of descending strength.

10. The method of claim 1, wherein the one or more physical characteristics are selected from a group consisting of a diameter, a thickness, and a sidewall angle.

11. The method of claim 1, wherein the time-dependent opto-acoustic signal is received from an opto-acoustic sensor from a group consisting of a SONUS® opto-acoustic metrology system and a MetaPULSE® opto-acoustic metrology system.

12. A method for use in manufacturing an interconnect structure in an integrated circuit (IC) device, the method comprising:
receiving a time-dependent opto-acoustic signal for a sample having the interconnect structure;
performing a Fourier analysis of the time-dependent opto-acoustic signal to generate a Fourier-transformed dataset;
identifying a plurality of local maxima from the Fourier-transformed dataset;
generating an estimate of one or more optical parameters for each identified local maximum in the plurality of local maxima;
fitting a mode to each of the local maxima in the plurality of local maxima based on the estimate of the one or more optical parameters;
iteratively generating a corrected dataset for each local maximum by subtracting the fitted mode for next strongest local maxima from a corrected data set for the previously stronger maximum;
extracting corrected optical parameters for each local maximum from the respective corrected dataset for each local maximum;
comparing the extracted optical parameters to a predicted physical model to quantify one or more physical characteristics of the interconnect structure; and
displaying the identified one or more physical characteristics.

13. The method of claim 12, wherein fitting the mode comprises fitting the mode to the form of:

$$A(i)e^{-\gamma(i)}\sin(f(i)t+\delta(i)),$$

wherein A represents an amplitude, t represents time, $\gamma$ represents an attenuation, $\delta$ represents a phase, and i is an index value for the local maximum.

14. The method of claim 13, wherein iteratively generating the corrected datasets is performed according to:

$$data(i)=data(i-1)-A(i)e^{-\gamma(i)}\sin(f(i)t+\delta(i))$$

wherein data(i) is the corrected data set for the ith local maximum.

15. The method of claim 12, wherein the one or more optical parameters include at least two of amplitude, frequency, phase, and attenuation.

16. The method of claim 12, wherein the one or more physical characteristics are selected from a group consisting of a diameter, a thickness, and a sidewall angle.

* * * * *